US012661309B2

(12) United States Patent
Santhanam et al.

(10) Patent No.: US 12,661,309 B2
(45) Date of Patent: Jun. 23, 2026

(54) PREPARATION AND EFFICACY OF TOOTH WHITENING TABLET INCLUDING SHMP

(71) Applicant: The Hershey Company, Hershey, PA (US)

(72) Inventors: Balaji Santhanam, Harrisburg, PA (US); Ian Fairs, Palmyra, PA (US)

(73) Assignee: THE HERSHEY COMPANY, Hershey, PA (US)

( * ) Notice: Subject to any disclaimer, the term of this patent is extended or adjusted under 35 U.S.C. 154(b) by 884 days.

(21) Appl. No.: 17/297,933

(22) PCT Filed: Nov. 29, 2019

(86) PCT No.: PCT/US2019/063878
§ 371 (c)(1),
(2) Date: May 27, 2021

(87) PCT Pub. No.: WO2020/113184
PCT Pub. Date: Jun. 4, 2020

(65) Prior Publication Data
US 2021/0393494 A1       Dec. 23, 2021

Related U.S. Application Data

(60) Provisional application No. 62/772,910, filed on Nov. 29, 2018.

(51) Int. Cl.
| | |
|---|---|
| *A61K 8/24* | (2006.01) |
| *A23G 3/36* | (2006.01) |
| *A23G 3/42* | (2006.01) |
| *A23G 3/50* | (2006.01) |
| *A61Q 11/00* | (2006.01) |

(52) U.S. Cl.
CPC ............... *A61K 8/24* (2013.01); *A23G 3/362* (2013.01); *A23G 3/42* (2013.01); *A23G 3/50* (2013.01); *A61Q 11/00* (2013.01); *A23V 2002/00* (2013.01)

(58) Field of Classification Search
CPC ... A61K 8/24; A23G 3/36; A23G 3/42; A23G 3/50; A61Q 11/00
See application file for complete search history.

(56) References Cited

U.S. PATENT DOCUMENTS

| | | | |
|---|---|---|---|
| 6,555,145 B1 | 4/2003 | Cherukuri | |
| 6,685,916 B1* | 2/2004 | Holme ..................... | A61K 8/22 424/490 |
| 8,496,913 B2 | 7/2013 | Kristiansen et al. | |
| 9,180,318 B2 | 11/2015 | Deng et al. | |
| 2006/0171907 A1* | 8/2006 | Scott ...................... | A61Q 11/00 424/53 |
| 2006/0210490 A1 | 9/2006 | Jakubowski et al. | |
| 2007/0148303 A1 | 6/2007 | Yeager et al. | |
| 2008/0131379 A1* | 6/2008 | Kristiansen ............ | A61K 8/345 424/48 |
| 2018/0325814 A1 | 11/2018 | Kumiega et al. | |

FOREIGN PATENT DOCUMENTS

| | | | | |
|---|---|---|---|---|
| WO | WO-0230378 A2 * | 4/2002 | ............... | A61K 8/33 |
| WO | WO-2007140286 A2 * | 12/2007 | .......... | A61K 8/0216 |
| WO | 2014152791 A1 | 9/2014 | | |

OTHER PUBLICATIONS

Rourke, Jeremy, "Five Ways to Naturally Whiten Your Teeth at Home", Star Dental, Dec. 13, 2018. (Year: 2018).*
International Search Report and Written Opinion for International Patent Application No. PCT/US2019/063878, mailed Mar. 24, 2020, 11 pages.
International Preliminary Report on Patentability for International Patent Application No. PCT/US2019/063878, dated Jun. 10, 2021, 8 pages.
Examination Report, CA Application No. 3,120,039, dated Oct. 11, 2024. Six pages.
First Office Action, China Application No. 201980079418.7, dated Apr. 2, 2024, 7 pages.
Office Action, KR Application No. 2021-7016796, dated Oct. 30, 2024. Nine pages.
Second Office Action, CN Application No. 201980079418.7, dated Dec. 3, 2024, 4 pages.
Third Office Action, CN Application No. 201980079418.7, dated Feb. 24, 2025, 5 pages.
Final Rejection for KR Application No. 2021-7016796, dated Sep. 17, 2025, four pages.
Decision of Rejection, CN Application No. 201980079418.7, dated Jun. 28, 2025, 5 pages.
Examination Report for CA Application No. 3,120,039, dated Jul. 16, 2025, four pages.
Office Action for MX Application No. MX/a/2021/006255 mailed on Nov. 20, 2025, 6 pages.

* cited by examiner

*Primary Examiner* — Lezah Roberts
(74) *Attorney, Agent, or Firm* — Jordan IP Law, LLC

(57) ABSTRACT

The present invention is directed to a confectionery capable of imparting tooth-whitening benefits to an end-user, the confectionery containing: sodium hexametaphosphate (SHMP), one or more sweeteners; and optionally a food-grade acid, such as citric acid. The present invention is also directed to a method of imparting tooth-whitening benefits to a consumer involving inserting the above-described confectionery into a consumer's mouth and allowing the confectionery to dissolve in the consumer's mouth, and repeating over a prolonged period of time.

19 Claims, 12 Drawing Sheets unstained enamel

Medium-stained enamel heavy-stained enamel

PREPARATION AND EFFICACY OF TOOTH WHITENING TABLET INCLUDING SHMP

CROSS REFERENCE

This application claims benefit of and priority to International Patent Application No. PCT/US2019/063878 filed Nov. 29, 2019, which claims benefit of and priority to U.S. Provisional Patent Application No. 62/772,910, filed Nov. 29, 2018, the contents of which are incorporated herein by reference in its entirety.

BACKGROUND

The present disclosure relates, in general, to confectionery products for tooth whitening that contain the ingredient sodium hexametaphosphate (SHMP).

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The disclosed embodiments satisfy the need in the art by providing an effective tooth whitening confectionery in tableted form. The confectionery is capable of imparting tooth-whitening benefits to an end-user over a course of usage. The present invention is also directed to a method of imparting tooth-whitening benefits to a consumer involving inserting the confectionery into a consumer's mouth and allowing the confectionery to dissolve in the consumer's mouth by act of sucking. Repetition of the dissolution step yields tooth whitening benefits.

Presently there are chewing gum based products which can remove tooth stains via the mechanical action of chewing or through the use of abrasive ingredients. However, many consumers do not care for chewing gum or are not able to chew gum, but would nevertheless like to obtain similar tooth whitening benefits using a tableted confectionery, such as a mint-based product.

SHMP is known to be an effective stain removal ingredient in toothpaste products. It has also been used in some chewing gum-based products to whiten teeth. U.S. Pat. No. 4,808,401 discloses efficacy of liquid and other preparations including SHMP and other linear polyphosphates when the pH is generally in the range of from about 4.5 to about 9 and typically from about 5.5 to 8. The pH is preferably in the range of from about 6 to about 8.0. The '401 Patent found it noteworthy that the compositions of the invention may be applied orally at a pH below 5 without substantially decalcifying or otherwise damaging dental enamel.

U.S. Pat. No. 5,037,637 also discloses efficacy of an antibacterial anti-plaque agent such as Triclosan with use of a polyphosphate salt, such as sodium hexametaphosphate, sodium tripolyphosphate, tetrasodium pyrophosphates. However, a dentrifice composition including among other things, tetrasodium pyrophosphate, but not including Tricolsan was found to not inhibit growth of *Bacteroides gingivalis*. See Table 3 of the '637 patent.

U.S. Pat. No. 6,685,916 claims novel combinations of at least two active components selected from peroxide compounds, polyphosphates, and anionic surfactants.

There is still a desire for an effective tableted, mint-based product.

There is a need for a tableted, mint-based product that provides effective tooth whitening benefits.

BRIEF DESCRIPTION OF THE DRAWINGS

The tooth whitening mints using sodium hexametaphosphate and method of use according to the present invention is further described with reference to the accompanying drawings, in which.

DETAILED DESCRIPTION OF THE PREFERRED EMBODIMENT

Figure 1:
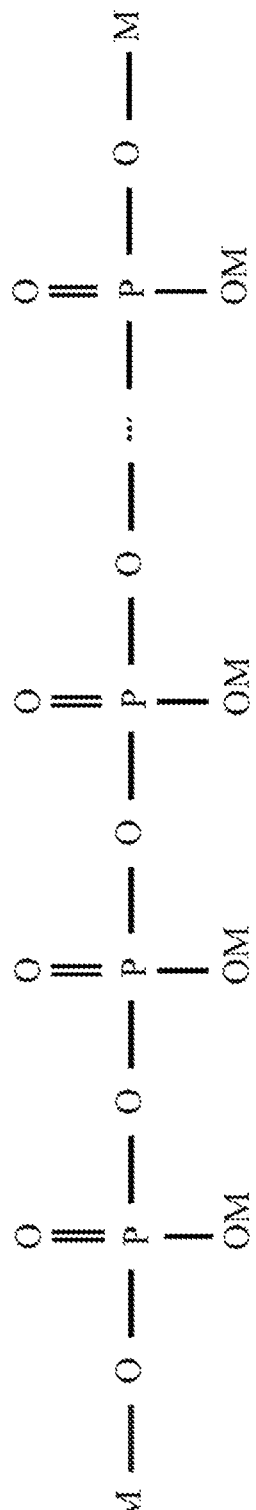
FIG. 1 is a chemical structure of a polyphosphate of the present disclosure, wherein the structure of SHMP is shown when M is sodium (Na)

The ensuing detailed description provides preferred exemplary embodiments only, and is not intended to limit the scope, applicability, or configuration of the herein disclosed inventions. Rather, the ensuing detailed description of the preferred exemplary embodiments will provide those skilled in the art with an enabling description for implementing the preferred exemplary embodiments in accordance with the herein disclosed invention. It is understood that various changes may be made in the function and arrangement of elements without departing from the spirit and scope of the invention, as set forth in the appended claims.

To aid in describing the invention, directional terms may be used in the specification and claims to describe portions of the present invention e.g., upper, lower, left, right, etc. These directional definitions are merely intended to assist in describing and claiming the invention and are not intended to limit the invention in any way. In addition, reference numerals that are introduced in the specification in association with a drawing figure may be repeated in one or more subsequent figures without additional description in the specification, in order to provide context for other features.

As used herein the terms "confectionery", "mint" and "confectionery product in tableted form" are used interchangeably to refer to a food product in the form of a tablet or lozenge, such as a breath mint.

Each percentage provided in the specification and claims should be understood to represent a percentage on a weight percentage basis unless specifically indicated otherwise.

In the past decade, tooth whitening products have grown exponentially and there are many non-food products such as toothpaste, gels, strips in the market that claim to provide whitening benefit. There are also chewing gum products in the food category that claim to provide such benefit. Chewing gum-based products primarily remove stains by mechanical action of chewing and/or use abrasive ingredients, or use peroxide based oxidizing agents to remove stain molecules. The use of abrasives or oxidizing agents can lead to enamel erosion. Many stain-removal ingredients may be found in the literature that are not abrasive or oxidizing in nature which, when added in a gum or tablet product can whiten teeth. Based on efficacy, one such ingredient to whiten teeth are polyphosphate compounds.

In literature, there exists many clinical studies using SHMP, a polyphosphate frequently used in Crest toothpaste formulations to remove extrinsic stains. SHMP is a linear polyphosphate which is widely used in many toothpaste formulations to remove extrinsic stains. It is also used in some chewing gum formulations to whiten teeth. The general formula for SHMP is $Na_{(n+2)}P_nO_{(3n+1)}$. The structure of SHMP is shown in FIG. 1 wherein M is sodium (Na).

SHMP is also referred as Graham's salt which is obtained when a liquid melt of sodium trimetaphosphate is quenched to form a glassy polymeric product. These salts are used in water softening applications where the calcium ions binds to the polyphosphate anions by exchanging sodium ions. Hence they have a strong affinity for calcium ions. It is hypothesized that SHMP removes stains and provides a whitening benefit due to the following mode of action: it is strongly attracted to calcium ions present in hydroxyapatite of the enamel; its ability to disrupt pellicle on the enamel and removes extrinsic stain; and it binds to the tooth surface to prevent new extrinsic stain.

Figure 2:
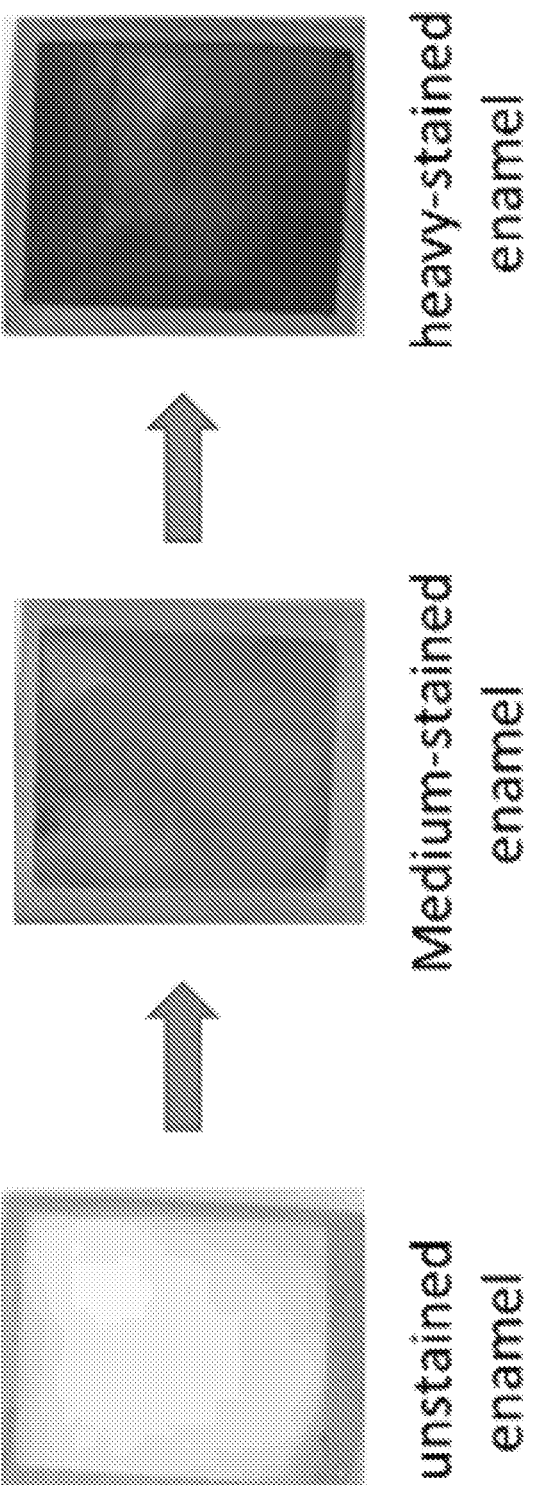
FIG. 2 is a digital image of the prestaining of bovine enamel specimens used to test the formulations of the present invention.

Disclosed herein are formulations containing SHMP in a tableted form having whitening efficacy as demonstrated using pre-stained bovine enamel slabs. Commercially available bovine enamel slabs were purchased from Theremetrics Inc. The slabs were prepared by immersing the enamel specimens in a staining broth containing coffee, tea and gastric mucin and air-drying the specimens. The gastric mucin (glycoprotein) was added to the straining broth to afford pellicle formation on the enamel surface. This mimics the dental pellicle formed by the glycoproteins present in the saliva. The broth immersion and air-drying procedure was repeated several times up to four days to afford a heavily-stained film containing the pellicle, as shown in FIG. 2.

Confectionary Composition

Sodium Hexametaphosphate (SHMP)

Polyphosphates have the general formula $M_{(n+2)}P_n O_{(3n+1)}$. Their anions are composed of chains in which each phosphorus atom is linked to its neighbors through two oxygen atoms, thus forming a linear, unbranched structure which may be represented schematically as shown in FIG. 1. It is also well understood that polyphosphate and metaphosphate are equivalent terms. Tripolyphosphates and tetrapolyphosphates are linear polyphosphates in contrast to cyclopolyphosphates with mono-compounds and dimeric compounds still called by orthophosphate and pyrophosphate, respectively. See The Second Edition of the Biochemistry of Inorganic Polyphosphates.

The general formula for SHMP is $Na_{(n+2)}P_nO_{(3n+1)}$. Preferably, the SHMP has a value of n ranging from 13 to 21. More preferably the SHMP has a value of 21.

The SHMP preferably comprises up to 10 percent by weight of the confectionery product. More preferably, the SHMP comprises from 6 to 10 percent by weight of the confectionery product. Most preferably the SHMP comprises from 7 to 9 percent by weight of the confectionery product.

Sweetener

The sweetener is preferably a sugar alcohol such as: xylitol, maltitol, mannitol, sorbitol, erythritol, arabitol, glycerol, lactitol, and the like. Preferably, the sweetener is sorbitol. Combinations of sugar alcohols may also be used. Secondary sweeteners may also be used. A preferred secondary sweetener is Aspartame.

The primary sweetener preferably comprises 60 percent to 100 percent by weight of the confectionery, more preferably from 85 percent to 95 percent by weight of the confectionery, most preferably from 80 percent to 90 percent by weight of the confectionery.

Optional Ingredients

The confectionery may optionally contain a food grade organic acid. A preferred food grade organic acid is citric acid. When present, the food grade organic acid comprises from 0.1 to 2.0 percent by weight of the confectionery. More preferably, the food grade organic acid comprises from 0.2 to 1.5 percent by weight of the confectionery. Most preferably, the food grade organic acid comprises from 0.7 to 1.01 percent by weight of the confectionery.

The confectionery may also contain one or more flavorants. Suitable flavorants include, but are not limited to, essential oils, spice and salt, conventionally used in confectionery products. Particularly preferred flavorants are those derived from mint oils such as peppermint, spearmint and the like because in combination with the sugar alcohol the resulting flavor composite yields a particularly cooling taste sensation.

The flavorants may be in solid form, such as a powder, crystalline, amorphous crystal, semicrystalline and the like. They may be in the form of liquids or they may be encapsulated or they may be spray dried. Additional flavors include those derived from essential oils, as well as those flavors characterized as either natural or artificial flavors. Examples include essential oils such as, without limitation, cinnamon, spearmint, peppermint, birch, and the like; natural or artificial fruit flavors, such as, without limitation, apple, pear, peach, strawberry, cherry, apricot, orange, lemon, watermelon, banana, and the like; bean-derived flavors such as, without limitation, coffee, cocoa powder and the like. The flavoring agent may be a spice commonly used in foods. Examples include chili powder, curry powder and the like. The flavorant may be a salt commonly used in the food arts, such as sodium chloride, potassium iodide, potassium chloride, sodium iodide and the like. In some embodiments, the product of the present invention contains one or more flavorants.

When present, flavorants are present in flavoring effective amounts known in the art. Flavorants preferably comprise 0.005 percent to 10 percent by weight of the confectionery, more preferably from 0.01 percent to 5 percent by weight of the confectionery, most preferably from 0.01 percent to 2 percent by weight of the confectionery.

The confectionery may optionally include one or more food additives normally found in confections such as preservatives, food grade processing agents and other food additives typically used in confectionery products. Examples include, but are not limited to, the food grade processing agent magnesium stearate and solubilizing agents such as medium chain triglycerides.

When present, food additives comprise up to 4 percent by weight of the confectionery, more preferably up to 2 percent by weight of the confectionery, most preferably up to 1 percent by weight of the confectionery.

EXAMPLES

Examples were conducted on bovine slabs using SHMP tablets with varying formulations. The SHMP level in these examples were fixed at a maximum acceptable level of 10.0% by weight based on likeability scores in a small sensory study.

Example 1

In this example, the stain-removal efficacy of the ingredient sodium hexametaphosphate (SHMP) in a tableted form is demonstrated using pre-stained bovine enamel slabs. The effects of pH and artificial saliva buffer medium on stain removal are also demonstrated.

Example 1 discloses a formulation and method for whitening enamel. The stain-removal efficacy of SHMP with two different molecular weights. The general formula for SHMP is $Na_{(n+2)}P_nO_{(3n+1)}$. Two grades of SHMP were used in the Example: Hexaphos SHMP granular grade with n=13 (SHMP-Hexa); and Glass H® SHMP long chain granular grade with n=21 (SHMP-LC). The whitening efficacy of SHMP ingredient alone was determined using Hexaphos grade. The effects of the saliva medium (artificial saliva vs. DI water) on stain removal were determined.

Preparation of SHMP & Control Tablets:

Both SHMP crystalline grade granular products were pulverized to small particle size with a Retsch ZM200 ball mill using a 20 micro mesh. The following batches were prepared (Table 1) with tablet weight of 1.8 g using a Manesty tablet press.

TABLE 1

SHMP and control (without SHMP) mints formulas for Example 1.

| | batch size | | |
| --- | --- | --- | --- |
| | 200 g | 400 g | wt % |
| | | Control mint | SHMP mint |
| SHMP conc | | 0% | 8% |
| sorbitol, flavor, color, Zinc gluconate, medium chain triglycerides, Mg. stearate | | 100% | 92% |
| | | Control mint | SHMP mint |
| SHMP concentration | | 0% | 8% |
| Sorbitol | | Balance to 100% | Balance to 100% |
| Magnesium Stearate | | 0.1% to 2.0% | 0.1% to 2.0% |
| Flavor and Color | | 0.1% to 10% | 0.1% to 10% |
| Breath freshening composition | | 0.1% to 4% | 0.1% to 4% |

Methodology:

Six treatments were performed with 3 bovine enamel slabs per treatment (2 medium stained and 1 heavy stained). The treatment conditions are listed in Table 2. The following treatment regimen was followed. The pre-stained enamel slabs were suspended in aqueous medium using a thin rod in a plastic container. An artificial saliva preparation—A 4 L stock solution of artificial saliva (AS) was prepared by adding HEPES (47.66 g, buffering agent), potassium chloride (8.95 g), potassium dihydrogen phosphate (0.39 g), calcium chloride dihydrate (0.71 g) and dissolving the salts in 4000 g of deionized (DI) water. The pH of the solution was adjusted from 5.2 to 7.0 by careful addition of IN NaOH solution.

Three mints and a magnetic stirrer bar were placed in the plastic container containing the slabs, and it was filled with 45 mL of solution (artificial saliva or DI water). A stock solution of 4.8 g SHMP in 500 mL of aqueous solution (artificial saliva or DI water) was prepared. For ingredient only treatment, 45 mL of the above solution was added per treatment cycle. The contents were stirred for 15 min inside an oven held at 37 degrees Celsius. It took approximately 10 min to dissolve the tablets.

After the treatment, the solution was emptied and the slab was rinsed with DI water and wiped with paper towel. The above treatment was repeated at a rate of 4 treatment cycles per day. The whiteness index was measured using Xrite spectrophotometer (L*a b) at the end of 28 and 56 cycles or treatments. Simultaneously, digital images of the enamel samples were also taken.

TABLE 2

Treatment conditions for the first set of experiments.

| Code | Treatment | Format | Aqueous medium |
| --- | --- | --- | --- |
| B | SHMP - Hexa | Ingredient only | Artificial saliva |
| A | SHMP - Hexa | Ingredient only | DI water |
| D | SHMP - Hexa (8%) | Compressed tablet | DI water |
| H | SHMP - Hexa (8%) | Compressed tablet | Artificial saliva |
| L | SHMP - LC | Compressed tablet | Artificial saliva |
| C | Control | Compressed tablet | Artificial saliva |

The term ΔE, known as the whitening index value, represents the change in color difference from baseline measurements. The L* a* b* values were measured by Xrite spectrophotometer which was calibrated every time prior use. These measurements were made at baseline, 28 cycles and at end of 56 cycles. Using the L* a* b* values, ΔE was calculated according to the formula as shown below.

$$\Delta E = \sqrt{(L_0^* - L_n^*)^2 + (a_0^* - a_n^*)^2 + (b_0^* - b_n^*)^2}$$

Figure 3:
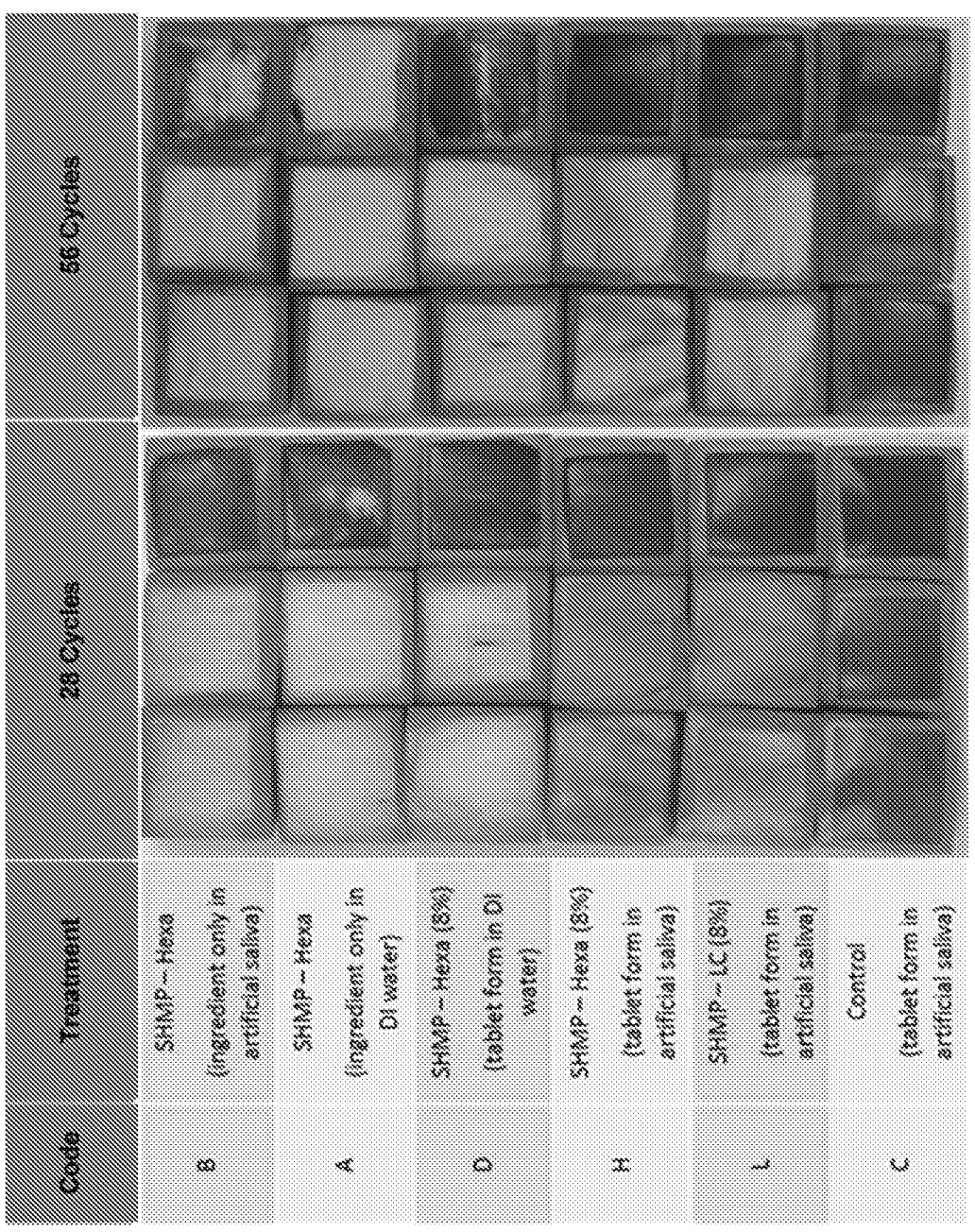
FIG. 3 is a digital image from Example 1 of bovine enamel slabs subject to six different treatment conditions using formulations of the present invention, wherein the left and middle columns under 28 cycles or 56 cycles are medium stained enamel slabs, wherein the right column under 28 cycles or 56 cycles are heavily stained enamel slabs.
Figure 4A:
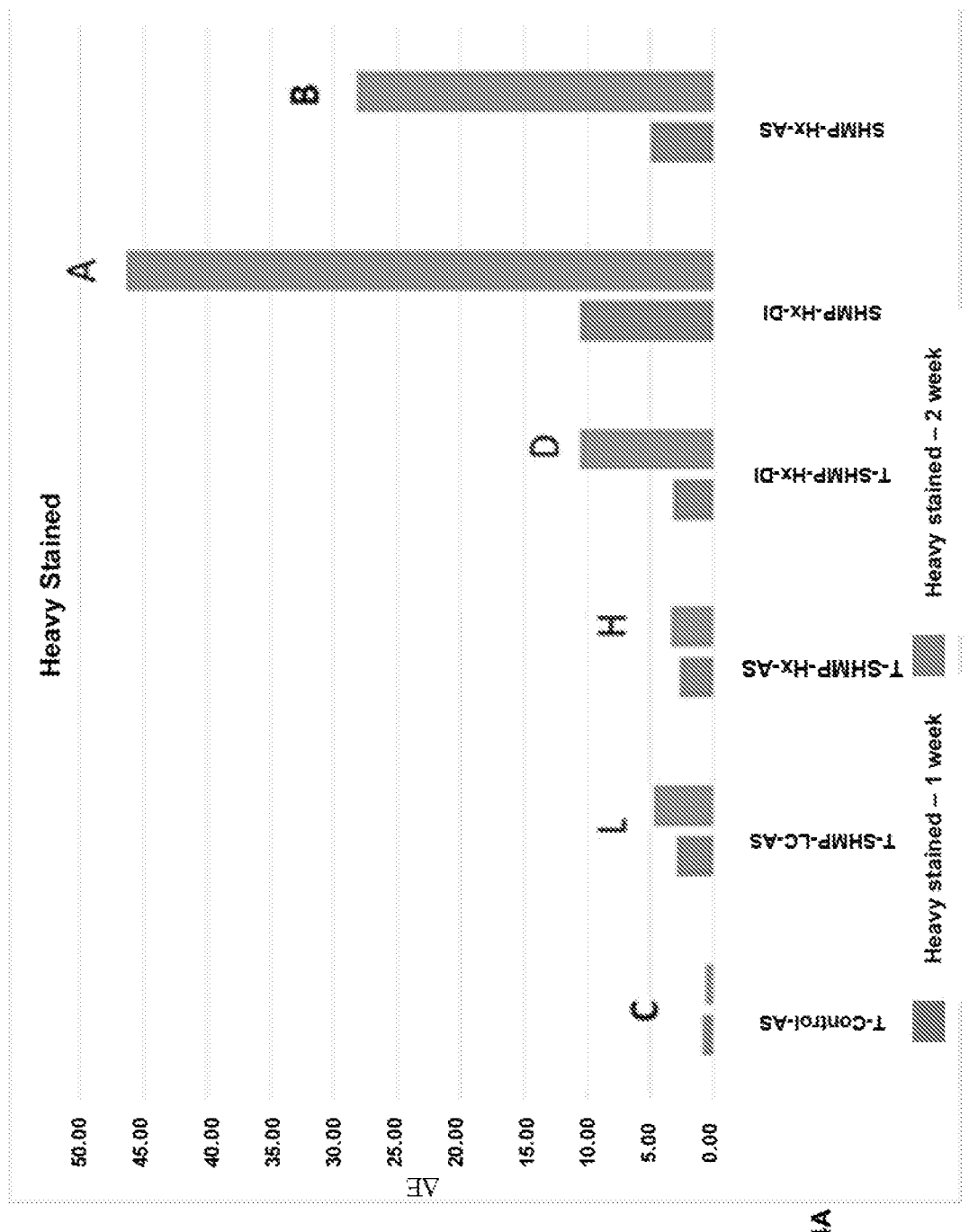
FIG. 4A is chart from Example 1 showing the change in color difference ($\Delta E$ values) of heavily stained (left) and medium stained (right) enamel slabs after 28 cycles (blue/left bar) and 56 cycles (orange/right bar)
Figure 4B:
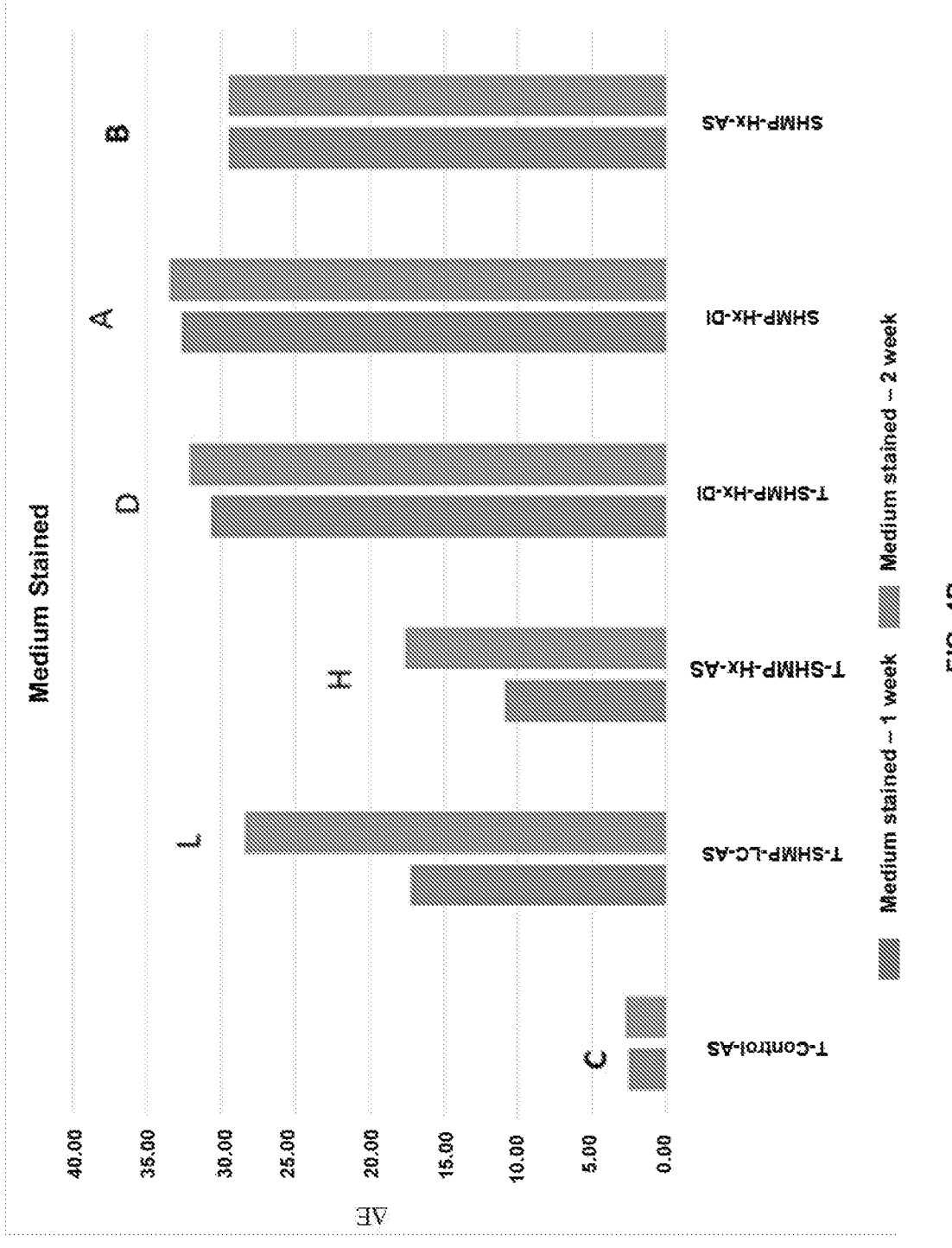
FIG. 4B is chart from Example 1 showing the change in color difference ($\Delta E$ values) of medium stained enamel slabs after 28 cycles (blue/left bar) and 56 cycles (orange/right bar)

L*$_0$, a*$_0$, b*$_0$—Baseline values
L*$_n$, a*$_n$, b*$_n$—n$^{th}$ cycle value Results:

Digital photographs of the enamel slabs are shown in FIG. 3 for the 6 treatment conditions at the end of 28 & 56 cycles. For each treatment condition, 2 medium-stained and 1 heavy-stained enamel blocks were used. ΔE values (change in color difference) is shown in FIG. 4 of heavy stained (left) and medium stained (right) enamel slabs after 28 cycles (blue) and 56 cycles (orange). Larger ΔE values represent a greater color change from stained to white.

Referring to FIGS. 3 and 4, the results indicate that the tablet containing SHMP and ingredient only (non-tableted) treatment clearly showed stain removal efficacy compared to baseline in medium stain tooth slab after 28 cycles of treatment. The ingredient only treatments (Codes B & A) performed better than tableted forms (Codes H, L & D) specifically in removing heavy stains. This suggest that the excipients in the tablet seem to interfere in the action of SHMP in removing stains. The ΔE values of treatments with tablets containing the stain removing ingredient SHMP LC (Code L) were higher than SHMP Hexa (Code H). Hence, the SHMP LC seems more effective in removing stains compared to SHMP Hexa. The artificial saliva medium played a negative effect compared to DI water in stain removal especially in the tablet form (Code H vs. Code D).

Example 2

Example 2 demonstrates the stain removal efficacy of SHMP mints at different pH levels (pH 5.8, 7.0, 8.0) using a phosphate buffer medium. This example also investigates the effect of buffer salts by comparing phosphate buffer and 4-(2-hydroxyethyl)-1-piperazineethanesulfonic acid (HEPES) buffer in artificial saliva on stain removal efficacy at a given pH.

Methodology:

The three phosphate buffer solutions (pH 5.8, 7.0, 8.0) were prepared using 0.2M NaH2PO4 and 0.2M Na2HPO4. The pH of the buffer solutions were adjusted using 0.1 M NaOH solution. Four treatments were performed with 3 bovine enamel slabs per treatment (2 medium stained and 1 heavy stained). The treatment conditions are listed in Table 3. The treatment protocol followed for Example 2 was similar to Example 1. The L* a* b* measurements were measured by Xrite spectrophotometer and digital images were taken at baseline, 28 cycles and at end of 56 cycles.

TABLE 3

Treatment conditions for Example 2.

| Code | Treatment | pH | Aqueous medium |
|------|-----------|-----|----------------|
| AS | SHMP LC - AS | 7.0 | Artificial saliva |
| 70 | SHMP LC - pH7 | 7.0 | Phosphate buffer |
| 58 | SHMP LC - pH5.8 | 5.8 | Phosphate buffer |
| 80 | SHMP LC - pH8.0 | 8.0 | Phosphate buffer |

Figure 5:
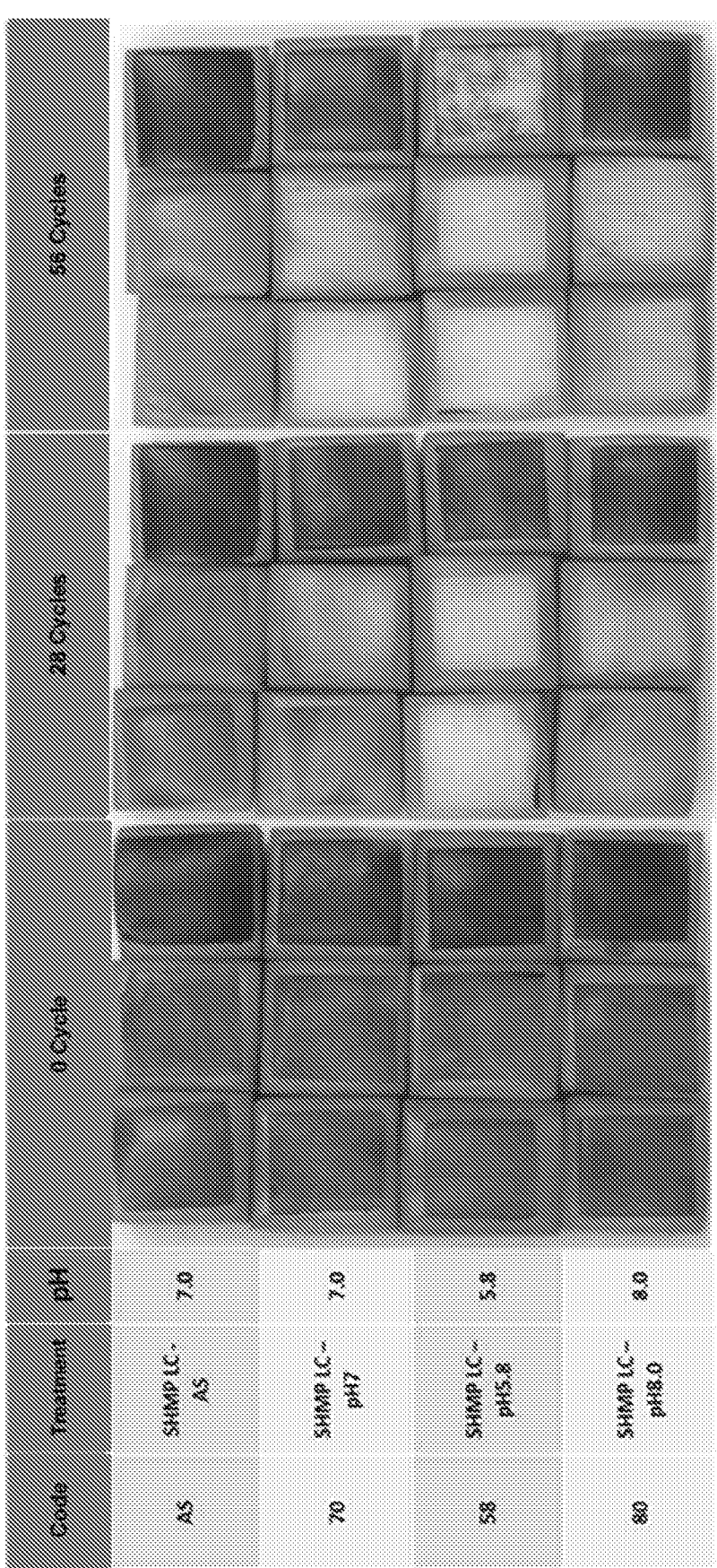
FIG. 5 is a digital image from Example 2 of bovine enamel slabs subject to four different treatment conditions using formulations of the present invention, wherein the left and middle columns under 0 cycles, 28 cycles, and 56 cycles are medium stained enamel slabs, wherein the right column under 0 cycles, 28 cycles, and 56 cycles are heavily stained enamel slabs.
Figure 6A:
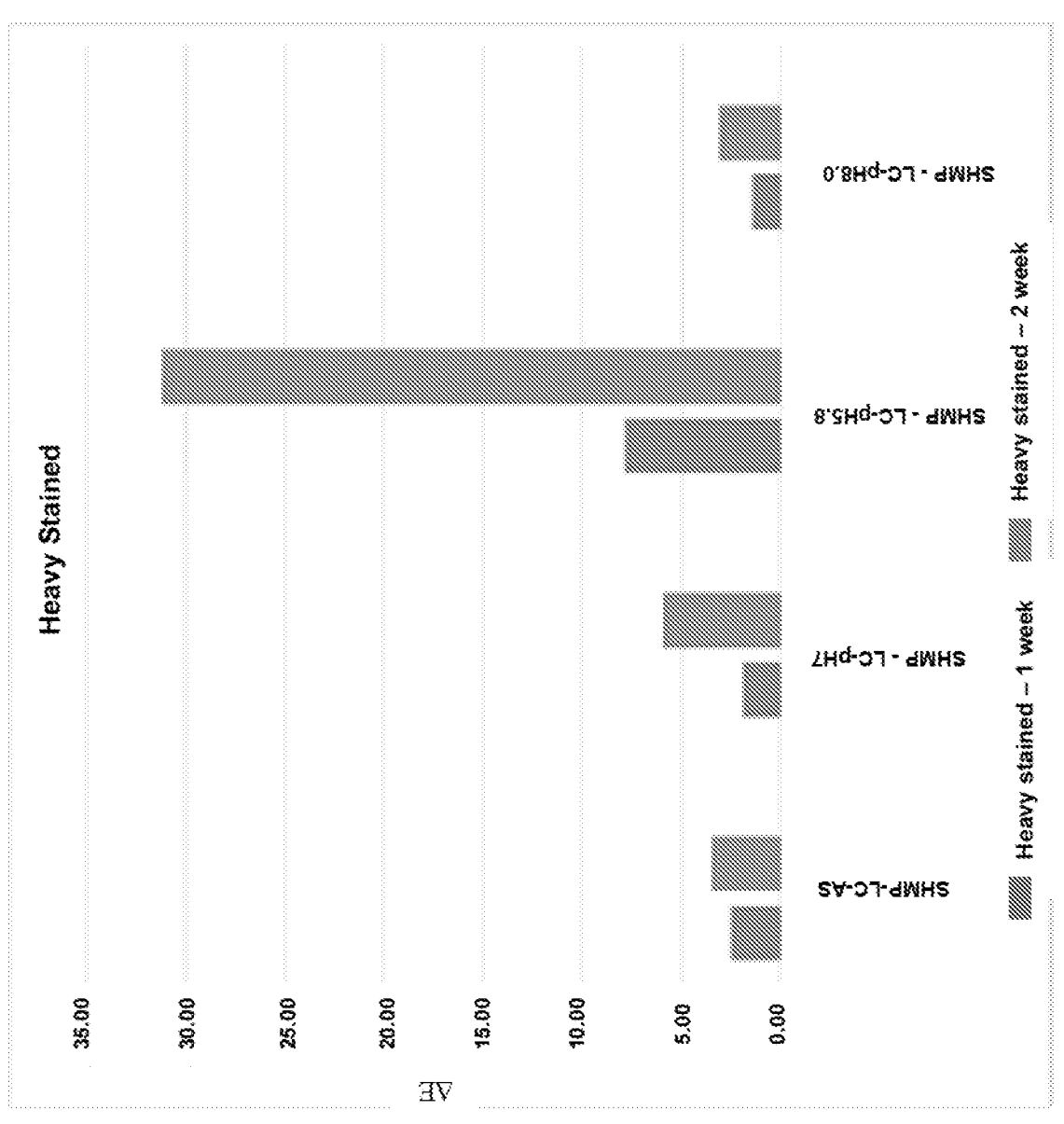
FIG. 6A is chart from Example 2 showing the change in color difference ($\Delta E$ values) of heavily stained (left) and medium stained (right) enamel slabs after 28 cycles (blue/left bar) and 56 cycles (orange/right bar)
Figure 6B:
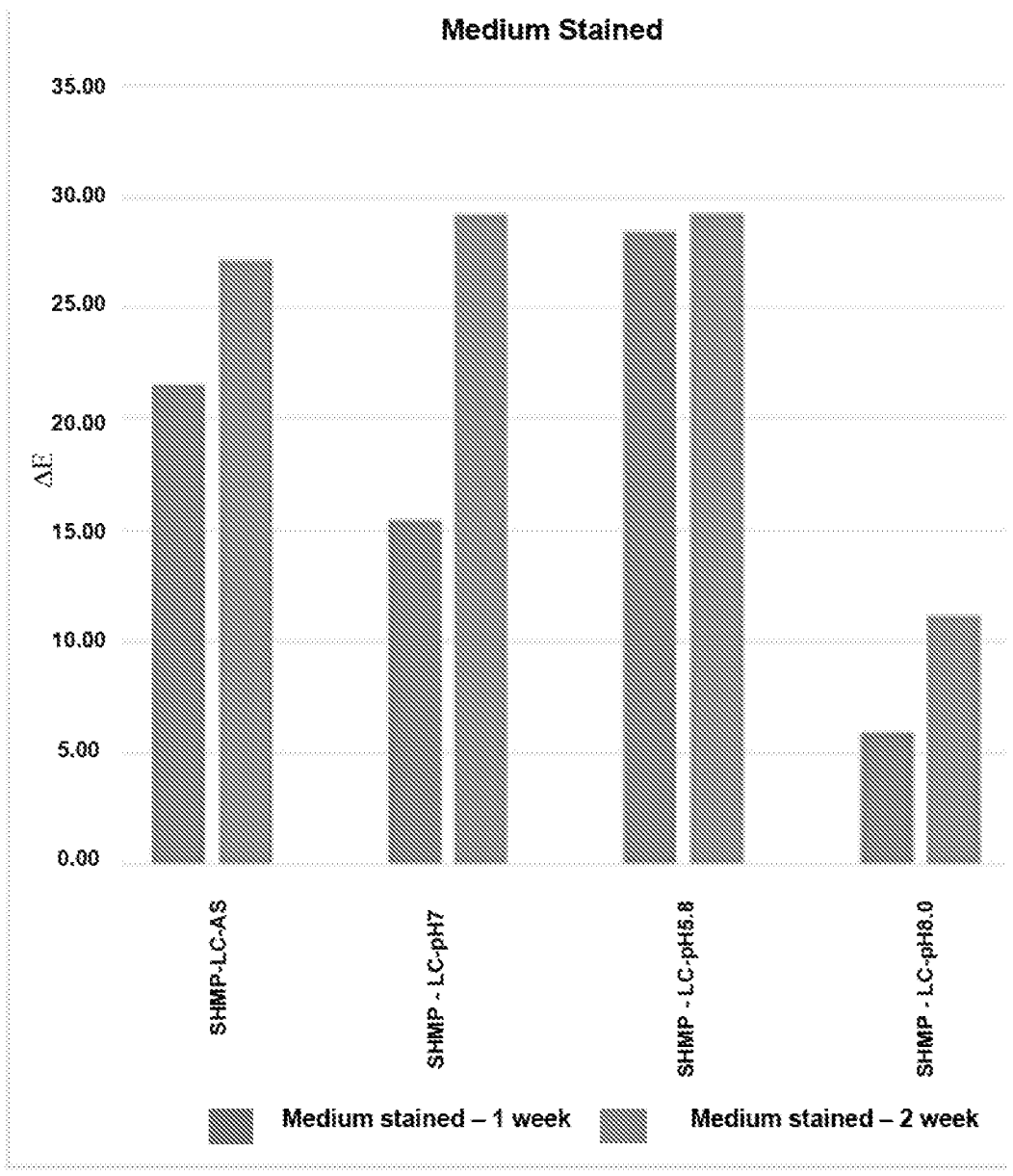
FIG. 6B is chart from Example 2 showing the change in color difference ($\Delta E$ values) of medium stained enamel slabs after 28 cycles (blue/left bar) and 56 cycles (orange/right bar)

Results:

FIG. 5 shows digital images of bovine enamel slabs for the 4 treatment conditions of Example 2. FIG. 6 shows the ΔE values (change in color difference) of heavy stained (left) and medium stained (right) enamel slabs after 28 cycles (blue) and 56 cycles (orange) in Example 2. Referring to FIGS. 5 and 6, based on ΔE values, the pH of the medium had a significant stain removing effect. Low pH treatment was better than high pH in removing stains from heavy and medium stained enamel slabs. Notably, for the pH 5.8 treatment, the stains from the heavy-stained enamel slabs were almost removed after 56 cycles (see FIG. 5) of treatment. The type of buffer solution had an effect on the stain removal. The phosphate buffer performed better than the (HEPES) buffer in artificial saliva as shown in the medium-stained enamel ΔE values.

In Example 1 and 2, the ingredient sodium hexametaphosphate (SHMP) in a tableted form demonstrated a significant capability to remove extrinsic stains compared to baseline treatment without the ingredient. Also, pH of the medium played a significant effect to remove stains as shown in Example 2.

Example 3

In Example 3, the stain-removal efficacy of the ingredient SHMP as function of concentration (0%, 2%, 5% and 8%) in a tableted form was evaluated using pre-stained bovine enamel slabs.

Methodology:

Artificial saliva was used as the medium for this example. The preparation of this medium is described in Example 1. Four treatments (0%, 3%, 5% and 8% SHMP) were performed with 3 medium stained bovine enamel slabs. The protocol followed for Example were similar to Example 1. The L* a* b* measurements were measured by Xrite spectrophotometer and digital images were taken at baseline, after 28 cycles and after 56 cycles.

Tablet Preparation:

The four treatment variants of each 500 g were prepared according the formula in Table 4 with a tablet weight of 1.8 g using the Manesty press similar to Example 1.

TABLE 4

Mints formulas for Example 3

| SHMP conc | 0% | 2% | 5% | 8% |
|-----------|-----|-----|-----|-----|
| sorbitol, flavor, color, Zinc gluconate, medium chain triglycerides, Mg. stearate | 100% | 98% | 95% | 92% |

Figure 7:
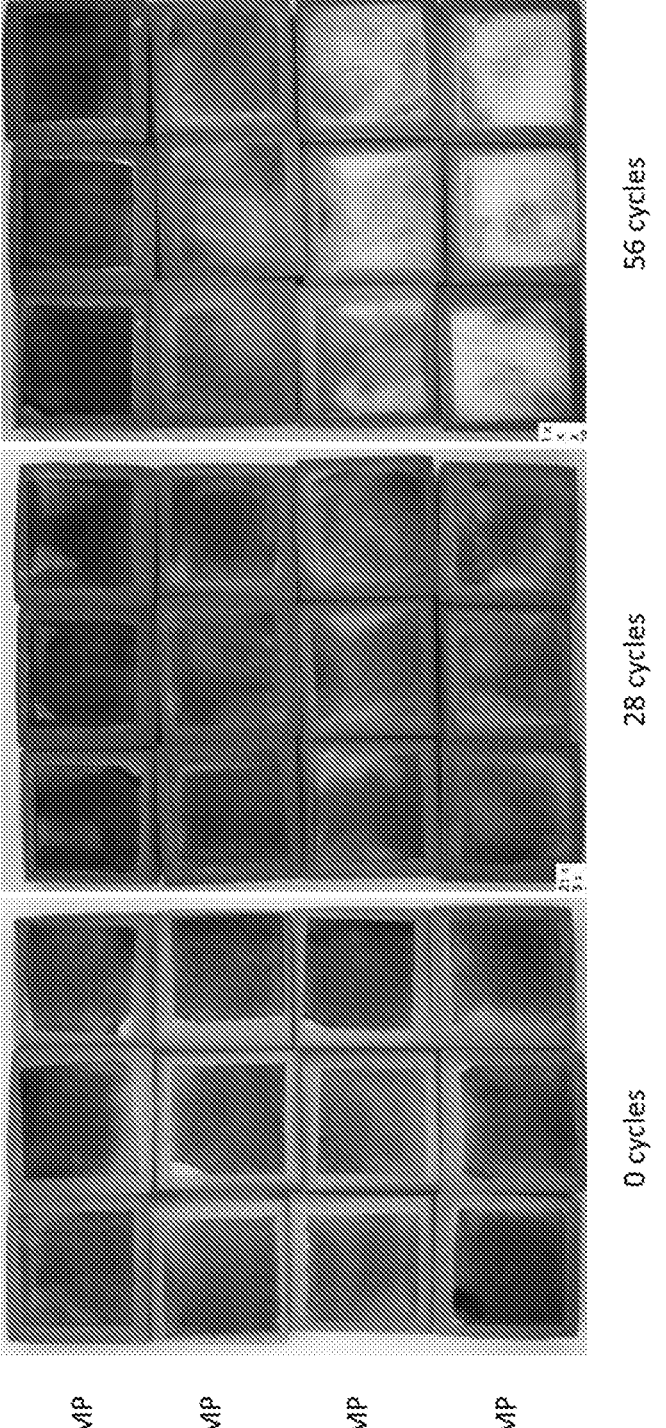
FIG. 7 is a digital image from Example 3 of bovine enamel slabs subject to four different treatment conditions using formulations of the present invention.
Figure 8:
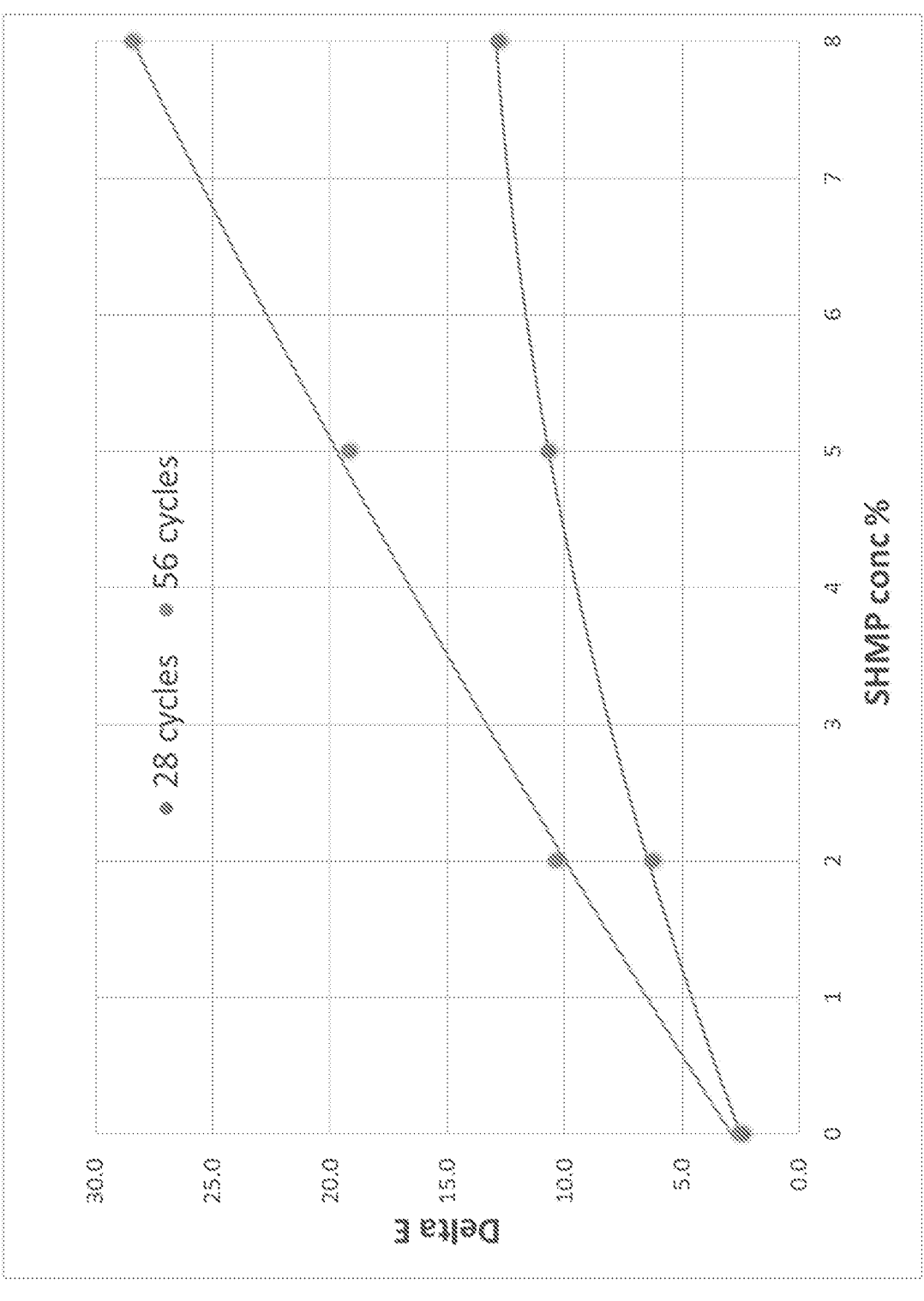
FIG. 8 is graph from Example 3 showing the change in color difference ($\Delta E$ values) medium stained enamel slabs after 28 cycles (blue/lower curve) and 56 cycles (orange/upper curve)

Results:

FIG. 7 shows digital images of bovine enamel slabs for the 4 treatment conditions of Example 3 at 0, 28 and 56 treatment cycles FIG. 8 shows ΔE values of medium stained enamel slabs after 28 cycles (blue) and 56 cycles (orange) are shown. Referring to FIG. 7, there is a linear relationship between SHMP concentration and the stain removal efficacy ΔE values. Based on ΔE, the SHMP concentration in the tablet had a significant stain removing effect after 28 and 58 cycles of treatment. For example, the whitening efficacy is reduced by 32% percent by dropping SHMP level from 8% to 5%.

Example 4

Example 4 demonstrates the stain removal efficacy of SHMP mints in a smaller format (0.8 g tablet versus 1.8 g tablet). It demonstrates the effect of the concentration of citric acid in a 0.8 tablet and the whitening efficacy of SHMP at low concentration with the addition of acid.

Methodology:

Artificial saliva was used as the medium for Example 4. The preparation of this medium is described in Example 1. Six treatments were performed with each treatment using 3 medium stained bovine enamel slabs. The protocol followed for Example 4 was similar to Example 1. The L* a* b* measurements were measured by Xrite spectrophotometer and digital images were taken at baseline, after 28 treatment cycles and after 56 treatment cycles.

Tablet Preparation:

Six treatment variants, labeled A through F, were prepared according the formulas in Tables 5 with a tablet weight of 1.8 g and 0.8 g using the Manesty press, similar to Example 1.

TABLE 5

Summary of treatment variants A through F, in Example 4

| Treatment code | Tablet weight (g) | SHMP % | serving size | SHMP/per serving (g) | Citric acid level | number of mints/cycle | Artificial saliva (mL) | SHMP conc per cycle (mg/mL) | mint conc per cycle (g/mL) |
|---|---|---|---|---|---|---|---|---|---|
| A | 1.8 | 8.0% | 1 | 0.144 | 0.00% | 3 | 45 | 9.60 | 0.12 |
| B | | 9.0% | 2 | 0.144 | 0.20% | 6 | 45 | 9.60 | 0.11 |
| C | | 5.6% | 2 | 0.090 | 0.72% | 6 | 45 | 5.97 | 0.11 |
| D | 0.8 | 5.6% | 2 | 0.090 | 1.01% | 6 | 45 | 5.97 | 0.11 |
| E | | 4.5% | 1 | 0.036 | 1.01% | 3 | 20 | 5.40 | 0.12 |
| F | | 0.0% | 2 | 0.000 | 1.01% | 6 | 45 | 0.00 | 0.11 |

Figure 9:
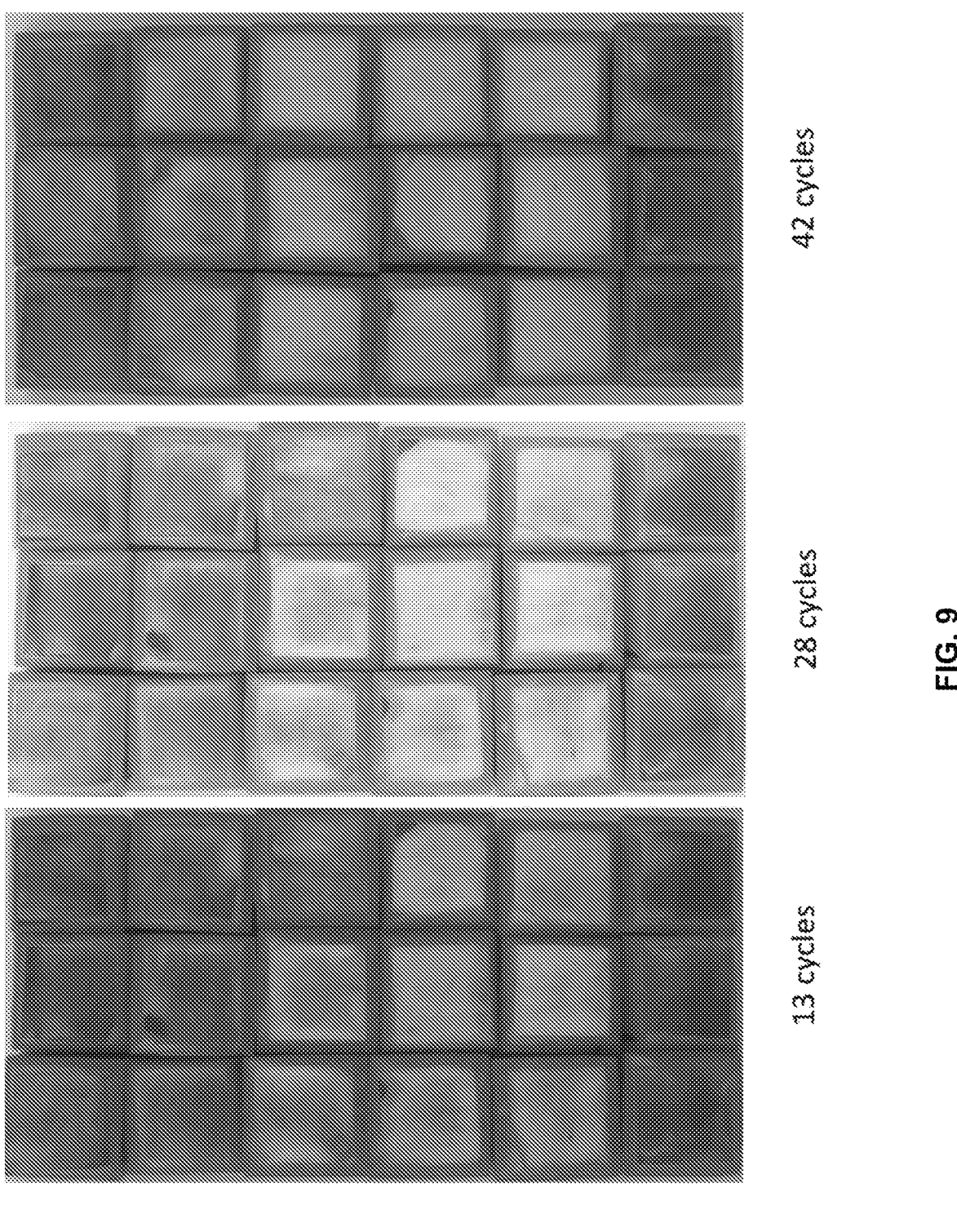
FIG. 9 is a digital image from Example 4 of bovine enamel slabs subject to six different treatment conditions using formulations of the present invention.
Figure 10:
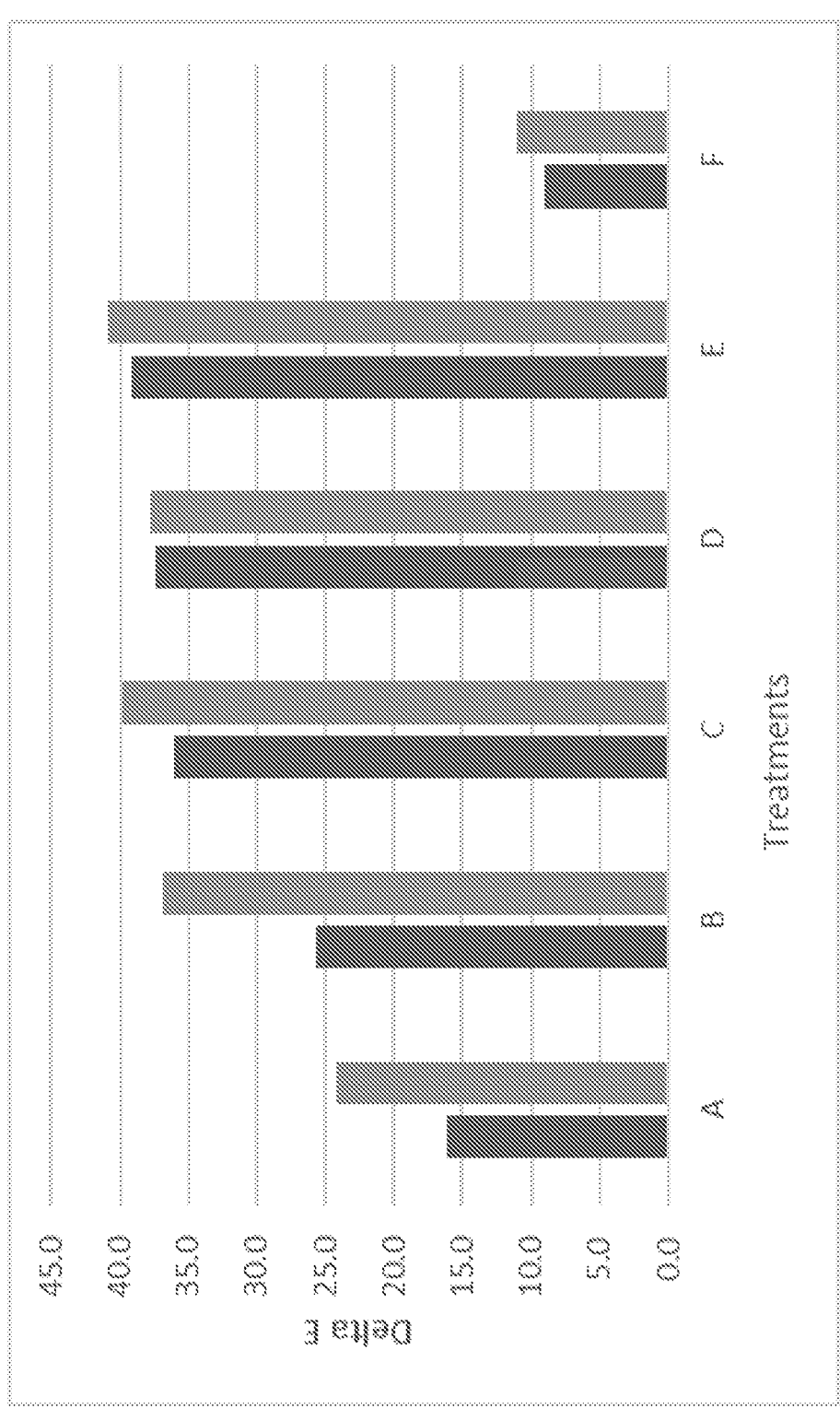
FIG. 10 is a chart from Example 4 showing the change in color difference ($\Delta E$ values) of heavily stained (left) and medium stained (right) enamel slabs after 28 cycles (blue/left bar) and 56 cycles (orange/right bar).

Results:

FIG. 9 shows digital images of bovine enamel slabs for the 4 treatment conditions of Example 4 after 13, 28 and 56 treatment cycles. FIG. 10 shows the ΔE values of medium stained enamel slabs after 28 cycles (blue) and 56 cycles (orange) as shown in FIG. 9. Treatments A and B demonstrate the stain removal efficacy of the same level of SHMP per treatment (0.144 g/serving) but with Treatment B in a smaller format (0.8 g tablet). Treatments C, D and E demonstrate the whitening efficacy of SHMP at low concentration with acid addition. Treatment F demonstrates the effect of an acid control sample with no SHMP.

Based on the ΔE values, Treatment B (0.8 g, 2 mints per serving) performed better than Treatment A (1.8 g, 1 mint per serving) though both treatments delivered the same amount SHMP per cycle. The difference in whitening efficiency between those treatments can be attributed to the small amount of citric acid added in treatment B formulation. Although treatments C, D & E had low levels of SHMP per cycle, they removed stains better than treatment B due to higher amounts of citric acid present in those formulations. Also, treatment E had the lowest amount of SHMP/cycle and its whitening efficacy was comparable to, or better than, treatments C&D, which had more SHMP per cycle. Acid treatment with no SHMP, Treatment F (control), had the smallest change in Delta E values or the least stain removal capability in this study. Treatment F did perform better than no SHMP & no acid control that was used in Example 3.

Example 4 demonstrates that addition of citric acid, or any food grade organic acid, can significantly improve the whitening efficacy of SHMP containing mints. It's known that linear sodium polyphosphates (SHMP) are not stable in acidic environments and they hydrolyze to form orthophosphates. It's possible that the addition of acid promotes the creation of orthophosphates, and that the whitening action of orthophosphate in combination with sodium polyphosphate is a better than sodium polyphosphate alone.

Example 5

Example 5 is an in vivo whitening study using SHMP in combination with citric acid in a tabulated mint product. Four testing variants were evaluated according to Table 6.

TABLE 6

Testing variants evaluated in Example 5

| 4 digit code | Variant |
|---|---|
| 1934 | control - 1 mint/serving |
| 8627 | 8% SHMP 1 mint/serving |

TABLE 6-continued

Testing variants evaluated in Example 5

| 4 digit code | Variant |
|---|---|
| 7989 | 9% SHMP - 2 mints/serving |
| 5529 | 4.5% SHMP 1% acid - 1 mint/serving |

TABLE 7

Composition of tablets used in Example 5

| | Mint A 5529 | Mint B 7989 | Mint C 1934 | Mint D 8627 |
|---|---|---|---|---|
| SHMP | 4.5% | 9.0% | 0.0% | 8.0% |
| citric acid | 1.0% | 0.2% | 0.0% | 0.0% |
| sorbitol, flavor, color, Zinc gluconate, medium chain triglycerides, Mg. stearate | 94.5% | 90.8% | 100.0% | 92.0% |

| | Mint A 5529 | Mint B 7989 | Mint C 1934 | Mint D 8627 |
|---|---|---|---|---|
| SHMP concentration | 4.5% | 9.0% | 0% | 8.0% |
| Citric acid | 1.0% | 0.2% | 0% | 0% |
| Sorbitol | Balance to 100% | Balance to 100% | Balance to 100% | Balance to 100% |
| Magnesium Stearate | 0.1% to 2.0% | 0.1% to 2.0% | 0.1% to 2.0% | 0.1% to 2.0% |
| Flavor and Color | 0.1% to 10% | 0.1% to 10% | 0.1% to 10% | 0.1% to 10% |

TABLE 7-continued

| Composition of tablets used in Example 5 | | | |
|---|---|---|---|
| Breath freshening composition | 0.1% to 4% | 0.1% to 4% | 0.1% to 4% 0.1% to 4% |

A controlled, double blind parallel study compared subjects provided with a whitening mint or placebo mint. Following an approximate 3-week pre-trial period to induce stain formation, a baseline examination was performed. Those subjects with sufficient extrinsic stain qualified for the trial. Extrinsic stain and Easyshade Advance 4.0 assessments at baseline were used for longitudinal comparisons and for assignment of subjects to treatment groups for the trial period. During the 8-week treatment period the subjects used their assigned mint product and brushed their teeth with the assigned toothbrush and dentifrice at home, and subjects recorded the treatments in a diary.

The overall investigation was divided into three parts: screening extrinsic stain and shade examinations supplemented with a medical questionnaire to identify suitable subjects; a three-week period to promote stain formation; and an eight-week trial period, proceeded by test product usage instruction, with clinical assessments (i.e. soft/hard tissue health, extrinsic stain, VITA Easyshade Advance 4.0 and digital images) at the start (baseline exam) and after 4 weeks (interim exam) and 8 weeks (final exam), in which subjects used the mint test product four times per day and brushed once daily with a commercial dentifrice. The mints were supplied in a white plastic bottle containing either 58 or 115 mints.

The following mint test products were used during the 8-week trial period:

A) Experimental Mint (#5529)

A sugarless strawberry flavored formulation comprising standard food approved ingredients. Subjects were instructed to use one mint (0.8 g) per usage occasion.

B) Experimental Mint (#7989)

A sugarless peppermint flavored formulation comprising standard food approved ingredients. Subjects were instructed to use two mints (0.8 g) per usage occasion.

C) Vehicle Control Breath Mint (#1934)

A sugarless peppermint flavored formulation comprising standard food approved ingredients. Subjects were instructed to use one mint (1.8 g) per usage occasion.

D) Experimental Mint (#8627)

A sugarless peppermint flavored formulation comprising standard food approved ingredients. Subjects were instructed to use one mint (1.8 g) per usage occasion.

At the beginning of the trial period all subjects successfully completing the pre-trial were assessed for oral soft/hard tissue health, extrinsic stain (Modified Lobene Stain Index) by a trained, experienced examiner and their tooth color assessed using the Easyshade Advance 4.0 on two lower anterior teeth. A standardized photograph of the anterior teeth was also taken on 10% of the subjects from each treatment group. Approximately 200 subjects were identified and selected according to the baseline inclusion criterion.

Results:

Table 8 below shows the improvements in the composite Modified Lobene Stain Index (MLSI) at the 4-week, and 8-week evaluation. Baseline MLSI results were comparable among the groups (F=0.90; p=0.441).

Referring to Table 8, results for Mints A, B, and D showed statistically significant improvements at both the 4-week (p<0.001) and 8-week evaluation (p<0.001) for composite MLSI. Both at the 4-week evaluation and 8-week evaluation the comparisons between Mints A, B, and D with Mint C showed statistical superiority in the improvements in stain removal for each of Mints A, B, and D when each was compared with the improvement seen by control Mint C (p<0.001: for all of A vs C, B vs C, and D vs C).

TABLE 8

| Modified Lobene Stain Index (Composite) | | |
|---|---|---|
| Summary of Results | 4 Weeks Reduction from Baseline (%) | 8 Weeks Reduction from Baseline (%) |
| Mint A 5529 | 49.8% | 57.2% |
| Mint B 7989 | 54.6% | 63.8% |
| Mint C 1934 | 8.4% | 6.4% |
| Mint D 8627 | 49.6% | 57.5% |

Although exemplary embodiments of the herein described device have been described in detail above, those skilled in the art will readily appreciate that many additional modifications are possible in the exemplary embodiments without materially departing from the novel teachings and advantages of the herein described device. Accordingly, these and all such modifications are intended to be included within the scope of the herein described device.

The invention claimed is:

1. A confectionery product, comprising:
a compressed tablet, which comprises:
a stain removal ingredient having a general formula (I):

$$Na_{(n+2)}P_nO_{(3n+1)} \tag{I}$$

wherein n is 13 or 21;
at least one sweetener; and
citric acid within a range of approximately 0.1% to approximately 4.0% by weight of the confectionery product, and
wherein the stain removal ingredient does not include an oxidizing agent.

2. The confectionery product of claim 1, wherein the stain removal ingredient is sodium polyphosphate, and wherein the sodium polyphosphate comprises from >0 to about 10 percent by weight of the confectionery product.

3. The confectionery product of claim 1, wherein the stain removal ingredient is within the range of approximately 0.1% to approximately 10% by weight of the confectionery product.

4. The confectionery product of claim 1, further comprising sorbitol, wherein sorbitol is the balance by weight of the confectionery product.

5. The confectionery product of claim 1, further comprising magnesium stearate, wherein magnesium stearate is within the range of approximately 0.1% by weight to approximately 2.0% by weight of the confectionery product.

6. The confectionery product of claim 1, further comprising flavor and color components, wherein the flavor and color components are within the range of approximately 0.1% by weight to approximately 10.0% by weight of the confectionery product.

7. The confectionery product of claim 1, further comprising breath freshening components, wherein the breath freshening components are within the range of approximately 0.1% by weight to approximately 10.0% by weight of the confectionery product.

13

14

8. The confectionery product of claim 1, further comprising:

sorbitol, wherein sorbitol is the balance by weight of the confectionery product, magnesium stearate, wherein magnesium stearate is within the range of approximately 0.1% by weight to approximately 2.0% by weight of the confectionery product, flavor and color components, wherein the flavor and color components are within the range of approximately 0.1% by weight to approximately 10.0% by weight of the confectionery product, breath freshening components, wherein the breath freshening components are within the range of approximately 0.1% by weight to approximately 10.0% by weight of the confectionery product, and wherein the stain removal ingredient is within the range of approximately 0.1% to approximately 10% by weight of the confectionery product.

9. A method for whitening tooth enamel of a mammal having stained tooth enamel, comprising:

a. dissolving in the mouth of the mammal, a confectionery product in compressed tablet form of claim 1.

10. The method of claim 9, further comprising:

b. repeating step (a) 2 or more times in a 24-hour period.

11. The method of claim 10, further comprising:

C. repeating step (b) for 2 or more times in a 24-hour period.

12. The confectionery product of claim 1, wherein the citric acid is a food grade citric acid within the range of approximately 0.1% to approximately 2.0% by weight of the confectionery product.

13. The confectionery product of claim 1, wherein the citric acid is a food grade citric acid within the range of approximately 0.2% to approximately 1.5% by weight of the confectionery product.

14. The confectionery product of claim 1, wherein the citric acid is a food grade citric acid within the range of approximately 0.7% to approximately 1.01% by weight of the confectionery product.

15. The method of claim 9, wherein the citric acid is a food grade citric acid within the range of approximately 0.1% to approximately 2.0% by weight of the confectionery product.

16. The method of claim 9, wherein the citric acid is a food grade citric acid within the range of approximately 0.2% to approximately 1.5% by weight of the confectionery product.

17. The method of claim 9, wherein the citric acid is a food grade citric acid within the range of approximately 0.7% to approximately 1.01% by weight of the confectionery product.

18. The confectionery product according to claim 2, wherein the sodium polyphosphate comprises from 4.5%-9.0% by weight of the confectionery product.

19. A confectionery product, comprising:

a compressed tablet consisting essentially of:

a stain removal ingredient having a general formula (I):

$$Na_{(n+2)}P_nO_{(3n+1)} \qquad \text{(I),}$$

wherein n is 13 or 21;

at least one sweetener; and a food grade citric acid, wherein the stain removal ingredient of formula (I) is in an amount of 4-10% by weight, and does not include an oxidizing agent, and the food grade citric acid is in an amount of 0.1-1.5% by weight.

\* \* \* \* \*